(12) United States Patent
Sondreaal

(10) Patent No.: US 11,432,952 B2
(45) Date of Patent: Sep. 6, 2022

(54) IMPLANTABLE MEDICAL DEVICES AND RELATED DELIVERY SYSTEMS

(71) Applicant: W. L. Gore & Associates, Inc., Newark, DE (US)

(72) Inventor: Matthew G. Sondreaal, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 380 days.

(21) Appl. No.: 15/980,232

(22) Filed: May 15, 2018

(65) Prior Publication Data

US 2018/0303646 A1 Oct. 25, 2018

Related U.S. Application Data

(63) Continuation of application No. 14/183,265, filed on Feb. 18, 2014, now Pat. No. 9,987,155.

(60) Provisional application No. 61/773,981, filed on Mar. 7, 2013.

(51) Int. Cl.
*A61F 2/966* (2013.01)
*A61F 2/07* (2013.01)
*A61F 2/97* (2013.01)
*A61F 2/95* (2013.01)
*A61F 2/958* (2013.01)

(52) U.S. Cl.
CPC ............. *A61F 2/9661* (2020.05); *A61F 2/07* (2013.01); *A61F 2/95* (2013.01); *A61F 2/97* (2013.01); *A61F 2002/9511* (2013.01); *A61F 2002/9583* (2013.01)

(58) Field of Classification Search
CPC ...... A61F 2/06; A61F 2/07; A61F 2/95; A61F 2/962; A61F 2/97; A61F 2002/9505; A61F 2002/9511; A61F 2002/9517; A61F 2002/9522; A61F 2002/9665; A61F 2/9661; A61F 2/9662
See application file for complete search history.

(56) References Cited

U.S. PATENT DOCUMENTS

| 6,203,550 | B1 | 3/2001 | Olson |
| 6,302,891 | B1 * | 10/2001 | Nadal ..................... A61F 2/962 |
| | | | 606/108 |
| 6,352,561 | B1 * | 3/2002 | Leopold .................... A61F 2/07 |
| | | | 623/1.11 |
| 6,733,521 | B2 | 5/2004 | Chobotov et al. |
| 6,911,039 | B2 | 6/2005 | Shiu |
| 6,974,471 | B2 | 12/2005 | Van Schie |
| 7,081,132 | B2 | 7/2006 | Cook |
| 7,147,661 | B2 | 12/2006 | Chobotov |
| 7,419,498 | B2 | 9/2008 | Opolski |

(Continued)

FOREIGN PATENT DOCUMENTS

| EP | 1474074 B1 | 4/2004 |
| EP | 1441668 B1 | 1/2008 |

(Continued)

*Primary Examiner* — Ashley L Fishback
*Assistant Examiner* — Christian D Knauss

(57) ABSTRACT

The present disclosure describes medical devices comprising implantable expandable implants, such as stent-grafts. Such devices can comprise a constraining line. The constraining line can surround the proximal end of the expandable implant, and assist in positioning and deployment of the expandable implant within the body of the patient.

15 Claims, 6 Drawing Sheets

(56) References Cited

U.S. PATENT DOCUMENTS

| | | |
|---|---|---|
| 7,655,034 B2 | 2/2010 | Mitchell et al. |
| 7,837,724 B2 | 11/2010 | Keeble |
| 7,938,851 B2 | 5/2011 | Olson |
| 7,976,575 B2 | 7/2011 | Hartley |
| 8,109,986 B2 * | 2/2012 | Styrc .................... A61F 2/2439 623/1.1 |
| 8,167,927 B2 | 5/2012 | Chobotov |
| 8,241,346 B2 | 8/2012 | Chobotov |
| 8,257,431 B2 | 9/2012 | Henderson |
| 8,262,671 B2 | 9/2012 | Osypka |
| 8,328,861 B2 | 12/2012 | Martin |
| 8,361,135 B2 | 1/2013 | Dittman |
| 8,480,725 B2 | 7/2013 | Rasmussen |
| 8,968,384 B2 | 3/2015 | Pearson |
| 9,060,895 B2 | 6/2015 | Hartley |
| 9,132,025 B2 | 9/2015 | Aristizabal |
| 9,254,204 B2 | 2/2016 | Roeder |
| 9,308,349 B2 | 4/2016 | Rezac |
| 9,498,361 B2 | 11/2016 | Roeder |
| 9,585,743 B2 | 3/2017 | Cartledge |
| 9,585,774 B2 | 3/2017 | Aristizabal |
| 9,681,968 B2 | 6/2017 | Goetz |
| 9,700,701 B2 | 7/2017 | Benjamin |
| 9,782,284 B2 | 10/2017 | Hartley |
| 9,937,070 B2 | 4/2018 | Skelton |
| 2002/0099436 A1 * | 7/2002 | Thornton ................ A61F 2/06 623/1.14 |
| 2003/0050684 A1 * | 3/2003 | Abrams ................ G06Q 10/00 623/1.11 |
| 2004/0122503 A1 * | 6/2004 | Campbell ................ A61F 2/97 623/1.12 |
| 2004/0176797 A1 | 9/2004 | Opolski |
| 2005/0119722 A1 | 6/2005 | Styrc |
| 2009/0299449 A1 * | 12/2009 | Styrc ................... A61F 2/95 623/1.11 |
| 2010/0049294 A1 * | 2/2010 | Zukowski ............... A61F 2/954 623/1.11 |
| 2011/0040366 A1 * | 2/2011 | Goetz ................... A61F 2/91 623/1.15 |
| 2012/0130474 A1 * | 5/2012 | Buckley ................ A61F 2/97 623/1.12 |
| 2012/0130475 A1 * | 5/2012 | Shaw ................... A61F 2/82 623/1.35 |
| 2017/0172724 A1 | 6/2017 | Cartledge |
| 2017/0281382 A1 | 10/2017 | Lostetter |

FOREIGN PATENT DOCUMENTS

| | | |
|---|---|---|
| EP | 1915113 B1 | 3/2010 |
| EP | 1358903 B1 | 2/2011 |
| EP | 2749251 B1 | 7/2016 |
| EP | 2956198 B1 | 11/2017 |

* cited by examiner

IMPLANTABLE MEDICAL DEVICES AND RELATED DELIVERY SYSTEMS

CROSS-REFERENCE TO RELATED APPLICATION

This application is a continuation of U.S. patent application Ser. No. 14/183,265, filed Dec. 18, 2014, now U.S. Pat. No. 9,987,155, granted Jun. 5, 2018, which claims the benefit of U.S. Provisional Application 61/773,981, filed Mar. 7, 2013, both of which are incorporated herein by reference in their entireties for all purposes.

FIELD

The present disclosure relates generally to implantable medical devices and, more specifically, to stent-grafts removably coupled to delivery devices.

BACKGROUND

Implantable medical devices are frequently used to treat the anatomy of patients. Such devices can be permanently or semi-permanently implanted in the anatomy to provide treatment to the patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and deployed to a treatment area using a catheter.

Typically, these implantable devices are attached to the catheter assembly and directed through the vasculature of the patient to the desired treatment area. Once the implantable device reaches the treatment area, the device is properly oriented and deployed to provide treatment. Such orientation and deployment is actuated by a physician using controls outside of the body of the patient. Accordingly, there is a need for medical devices with improved maneuverability and positioning within the vasculature of the patient.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

DETAILED DESCRIPTION OF THE ILLUSTRATED EMBODIMENTS

Figure 1:
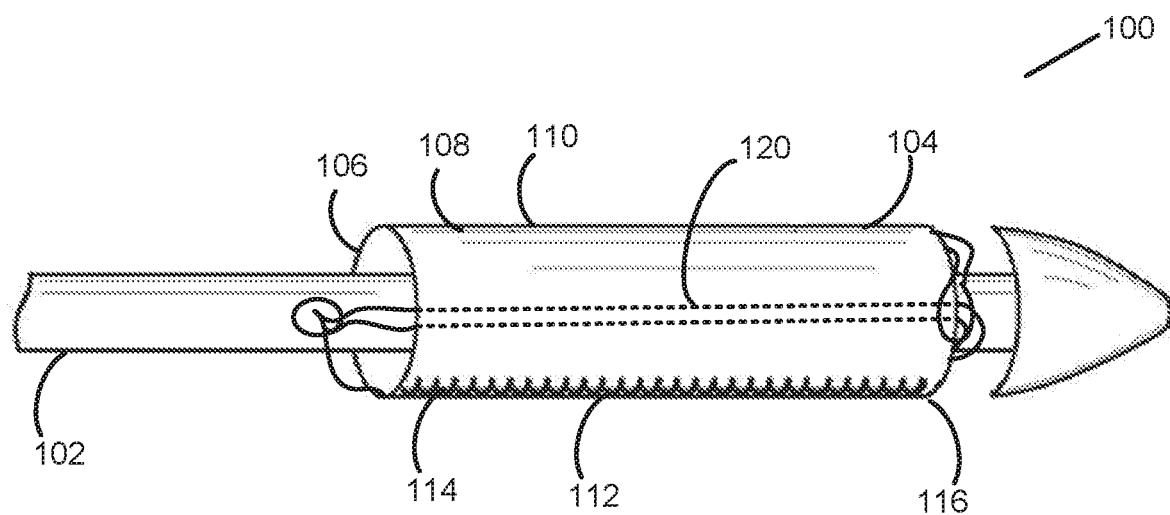
FIG. 1 illustrates a perspective view of a medical device in accordance with the present disclosure.

Persons skilled in the art will readily appreciate that various aspects of the present disclosure may be realized by any number of methods and systems configured to perform the intended functions. Stated differently, other methods and systems can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting.

As used herein, "medical devices" can include, for example, stents, grafts, stent-grafts, filters, valves, occluders, markers, mapping devices, therapeutic agent delivery devices, prostheses, pumps, bandages, and other endoluminal and implantable devices that are implanted, acutely or chronically, in the vasculature or other body lumen or cavity at a treatment region.

The medical devices, support structures, coatings, and covers, described herein, can be biocompatible. As used herein, "biocompatible" means suited for and meeting the purpose and requirements of a medical device, used for long- or short-term implants or for non-implantable applications. Long-term implants are generally defined as devices implanted for more than about 30 days, while short-term implants are generally defined as devices implanted for less than about 30 days.

As used herein, "proximal" indicates a position closer to the heart of the patient, or to a portion of a device that, when implanted, is closer to the heart of the patient than another portion of the device. "Distal" indicates a position farther from the heart of the patient, or to a portion of a device that, when implanted, is farther from the heart of the patient than another portion of the device. Implanted devices having tubular or rod-like shape comprise a distal end, a distal portion, a medial portion, a proximal portion, and a proximal end moving from the end farthest from the heart to the end closest to the heart.

As used herein, a "sleeve" can include any enclosure constraining an expandable device. In various embodiments, a sleeve can comprise a sheet of material wrapped around an expandable device in a collapsed, intermediate, or treatment configuration.

As used herein, the term "constrain" means: (i) to limit expansion, occurring either through self-expansion or assisted expansion, of the diameter of an expandable implant; or (ii) to cover or surround, but not otherwise restrain, an expandable implant such as for storage or biocompatibility reasons and/or to provide protection to the expandable implant and/or the vasculature.

As used herein, "deployment" refers to the actuation of a device at a treatment site, such as for example, the release and/or removal of a sleeve from a self-expanding device to allow the device to expand. The deployment process can be in stages, such as for example, a first stage comprising the release of a sleeve to a configuration suitable to constrain the expandable device only to an intermediate configuration, and a second stage comprising the removal of the sleeve altogether from the device.

Various embodiments of the present disclosure comprise a catheter assembly configured to deliver an expandable implant to a treatment area of the vasculature of a patient. In accordance with embodiments of the disclosure, an expandable implant, such as a stent-graft, is constrained by one or more sleeves concentrically surrounding the expandable implant. The expandable implant can be maintained in a desired orientation and/or position relative to the catheter assembly by a constraining line. Benefits of expandable implants in accordance with the present disclosure can include improved maneuverability of the expandable implant within the vasculature of a patient, and improved deployment characteristics.

With initial reference to FIG. 1, a catheter assembly 100 in accordance with the present disclosure is illustrated. Catheter assembly 100 comprises a catheter shaft 102. An expandable implant 104 is positioned at a proximal end of and removably coupled to catheter shaft 102 by a constraining line 120. Expandable implant 104 is concentrically surrounded by at least one constraining sleeve, such as sleeve 110.

In various embodiments, expandable implant 104 comprises a stent-graft. Conventional stent-grafts are designed to dilate from their delivery diameter, through a range of intermediary diameters, up to a maximum, often pre-determined functional diameter, and generally comprise one or more stent components with one or more graft members displaced over and/or under the stent.

In various embodiments, expandable implant 104 comprises one or more stents 106. In various embodiments, stent 106 comprises a biocompatible material. For example, stent 106 can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol, and biologically derived materials such as bovine arteries/veins, pericardium and collagen. Stent 106 can also comprise bioresorbable materials such as poly(amino acids), poly(anhydrides), poly(caprolactones), poly(lactic/glycolic acid) polymers, poly(hydroxybutyrates) and poly(orthoesters). Any material that is biocompatible and provides adequate support for expandable implant 104 is in accordance with the present disclosure.

Stent 106 can comprise, for example, various configurations such as joined rings, cut tubes, wound wires (or ribbons) or flat patterned sheets rolled into a tubular form. However, any configuration of stent 106 that can be implanted in and provide support to the vasculature of a patient is in accordance with the present disclosure.

In various embodiments, stent 106 can comprise one or more anchors 116. For example, one or more anchors 116 can be located at or near the proximal end of stent 106. In such configurations, anchors 116 can engage and attach to the vasculature of the patient to maintain expandable implant 104 in a desired position within the vasculature. The use of any number and configuration of anchors 116 is within the scope of the present disclosure.

In various embodiments, expandable implant 104 comprises a graft member 108. Graft member 108 can comprise a biocompatible material that provides a lumen for blood flow within a vasculature. For example, graft member 108 can comprise a composite material having a flexible matrix. In such configurations, the flexible matrix can comprise, for example, expanded polytetrafluoroethylene (ePTFE), pebax, polyester, polyurethane, fluoropolymers, such as perfouorelastomers and the like, polytetrafluoroethylene, silicones, urethanes, ultra high molecular weight polyethylene, aramid fibers, silk, and combinations thereof. Other flexible matrices can include high strength polymer fibers such as ultra high molecular weight polyethylene fibers (e.g., Spectra®, Dyneema Purity®, etc.) or aramid fibers (e.g., Technora®, etc.). Any graft member 108 that provides a sufficient lumen for blood flow within a vasculature is in accordance with the present disclosure.

In various embodiments, graft member 108 can comprise a composite material having a flexible matrix and an elastomeric component. An elastomeric component can comprise, for example, a perfluoroalkylvinylether (PAVE), such as perfluoromethylvinylether (PMVE) as described in U.S. Pat. No. 7,462,675 (hereby incorporated by reference), perfluoroethylvinylether (PEVE), or perfluoropropylvinylether (PPVE). Other biocompatible polymers which can be suitable for use in embodiments can include, but are not limited to, the group of urethanes, silicones, copolymers of siliconurethane, styrene.isobutylene copolymers, polyisobutylene, polyethylene-co-poly(vinyl acetate), polyester copolymers, nylon copolymers, fluorinated hydrocarbon polymers and copolymers or mixtures of each of the foregoing. In such configurations, the flexible matrix is imbibed with the elastomeric component. However, any elastomeric component that is biocompatible and can be imbibed by a suitable flexible matrix is in accordance with the present disclosure.

With reference to FIG. 1, expandable implant 104 can be delivered to the treatment area of a patient by a catheter assembly 100. In various embodiments, expandable implant 104 is delivered into the body of a patient via catheter shaft 102. In such embodiments, expandable implant 104 can be collapsed and/or compressed and positioned at the proximal end of catheter shaft 102. Expandable implant 104 can then be navigated through the body of the patient to the treatment area.

In various embodiments, expandable implant 104 can comprise a radially collapsed configuration suitable for delivery to the treatment area of the vasculature of a patient. Expandable implant 104 can be constrained in a radially collapsed configuration and mounted onto a delivery device such as catheter shaft 102. The diameter of the expandable implant 104 in the collapsed configuration is small enough for the implant to be delivered through the vasculature to the treatment area. In various embodiments, the diameter of the collapsed configuration is small enough to minimize the crossing profile of catheter assembly 100 and minimize tissue damage to the patient. In the collapsed configuration, the expandable implant 104 can be guided by catheter shaft 102 through the vasculature. Once expandable implant 104 is in position in the treatment area of the vasculature, it can be expanded to a radially expanded configuration.

In various embodiments, expandable implant 104 can comprise a radially expanded configuration suitable for implanting the device in the treatment area of a patient's vasculature. In the expanded configuration, the diameter of expandable implant 104 can be approximately the same as the vessel to be repaired. In other embodiments, the diameter of expandable implant 104 in the expanded configuration can be slightly larger than the vessel to be treated to provide a traction fit within the vessel.

In various embodiments, expandable implant 104 can comprise a self-expandable device, such as a self-expandable stent-graft. Such devices dilate from a radially collapsed configuration to a radially expanded configuration when unrestrained. In other embodiments, expandable implant 104 can comprise a device that is expanded with the assistance of a secondary device such as, for example, a balloon. In yet other embodiments, catheter assembly 100 can comprise a plurality of expandable implants 104. The use of a catheter assembly with any number of expandable implants is within the scope of the present disclosure.

Various medical devices in accordance with the disclosure comprise a sleeve or multiple sleeves. The sleeve or sleeves can constrain an expandable implant device in a collapsed configuration for endoluminal delivery of the implant to a treatment portion of the vasculature of a patient. For example, as illustrated in FIG. 1, catheter assembly 100 comprises sleeve 110. Sleeve 110 surrounds and constrains expandable implant 104 to a reduced diameter.

After delivery of the expandable implant to the treatment portion of the vasculature of the patient, the sleeve or sleeves can be unconstrained in order to allow the expandable implant to expand to its functional diameter and achieve the desired therapeutic outcome. In various embodiments, the sleeve or sleeves can remain implanted while not interfering with the expandable implant. In other embodiments, the sleeve or sleeves can be removed from the body of the patient after successful deployment of the expandable implant.

In various embodiments, sleeves such as sleeve 110 can be formed from a sheet of one or more materials wrapped or folded about the expandable implant. While the illustrative embodiments herein are described as comprising one or more tubular sleeves, sleeves of any non-tubular shape that corresponds to an underlying expandable implant or that are otherwise appropriately shaped for a given application are also within the scope of the present disclosure.

In various embodiments, sleeves are formed by wrapping or folding the sheet of material(s) such that two parallel edges of the sheet are substantially aligned. Said alignment may or may not be parallel to or coaxial with the catheter shaft of a catheter assembly. In various embodiments, the edges of the sheet of material(s) do not contact each other. In other embodiments the edges of the sheet of material(s) contact each. Any manner of forming a sleeve from a sheet of material is within the scope of the present disclosure.

In various embodiments, sleeves comprise materials similar to those used to form a graft member. For example, a precursor flexible sheet used to make the sleeve can be formed from a flattened, thin wall ePTFE tube. The thin wall tube can incorporate "rip-stops" in the form of longitudinal high strength fibers attached or embedded into the sheet or tube wall.

The sheet of material(s) used to form the sleeve(s) can comprise a series of openings, such that the openings extend from one edge of the sheet to the other. In such configurations, a coupling member can be woven or stitched through the series of openings in the sheet of material(s), securing each of the two edges together and forming a tube. For example, in FIG. 1, catheter assembly 100 comprises a coupling member 112 that engages with a plurality of holes 114 and secures the edges of sleeve 110 such that sleeve 110 maintains expandable implant 104 in a reduced diameter.

In various embodiments, when the expandable implant is in position within the vasculature, coupling member 112 can be disengaged from the sleeve or sleeves from outside of the body of the patient, which allows the sleeve(s) to open and the expandable implant to expand. As discussed above, the expandable implant can be self-expanding, or the implant can be expanded by a device, such as a balloon.

Coupling member 112 can comprise, for example, a woven fiber. In other embodiments, the coupling member can comprise a monofilament fiber. Any type of string, cord, thread, fiber, or wire that is capable of maintaining a sleeve in a tubular shape is within the scope of the present disclosure.

The coupling member or members can be disengaged from the sleeve or sleeves by a mechanical mechanism operated from outside of the body of the patient. For example, coupling member 112 can be disengaged by applying sufficient tension to coupling member 112. In another example, a dial or rotational element of a catheter handle can be attached to coupling member 112 outside of the body. Rotation of the dial or rotational element can provide sufficient tension to, displace and disengage coupling member 112.

In various embodiments, disengaging a single coupling member that closes a single sleeve from the sleeve allows the expandable device to be fully expanded. For example, with reference to FIG. 1 catheter assembly 100 can be used to deliver an expandable implant 104 to a treatment area of a vasculature. In such configurations, sleeve 110 circumferentially surrounds expandable implant 104 and constrains it to a collapsed configuration. Once expandable implant 104 is in position relative to the treatment area, coupling member 112 is disengaged from sleeve 110 and sleeve 110 is released, allowing expandable implant 104 to expand from a collapsed configuration to a larger diameter.

In various embodiments, catheter assembly 100 further comprises a constraining line 120. Constraining line 120 can, for example, assist in securing expandable implant 104 to catheter shaft 102. In various embodiments, constraining line 120 can be positioned on or near the proximal end of expandable implant 104. In other embodiments, constraining line 120 can be positioned at or near the distal, or at any position between the proximal and distal end, of expandable implant 104. Constraining line 120 can interact with expandable implant 104 and assist in maintaining a desired position and orientation of expandable implant 104 in relation to catheter shaft 102. In such embodiments, constraining line 120 can improve maneuverability of expandable implant 104 relative to the treatment area of the patient by, for example, allowing an operator to displace and orient expandable implant 104 within the vasculature of a patient even after the implant has been partially or fully expanded. Further, constraining line 120 can constrain and prevent the proximal end of expandable implant 104 from contacting and/or engaging the vasculature until full and final deployment is desired.

Figure 2:
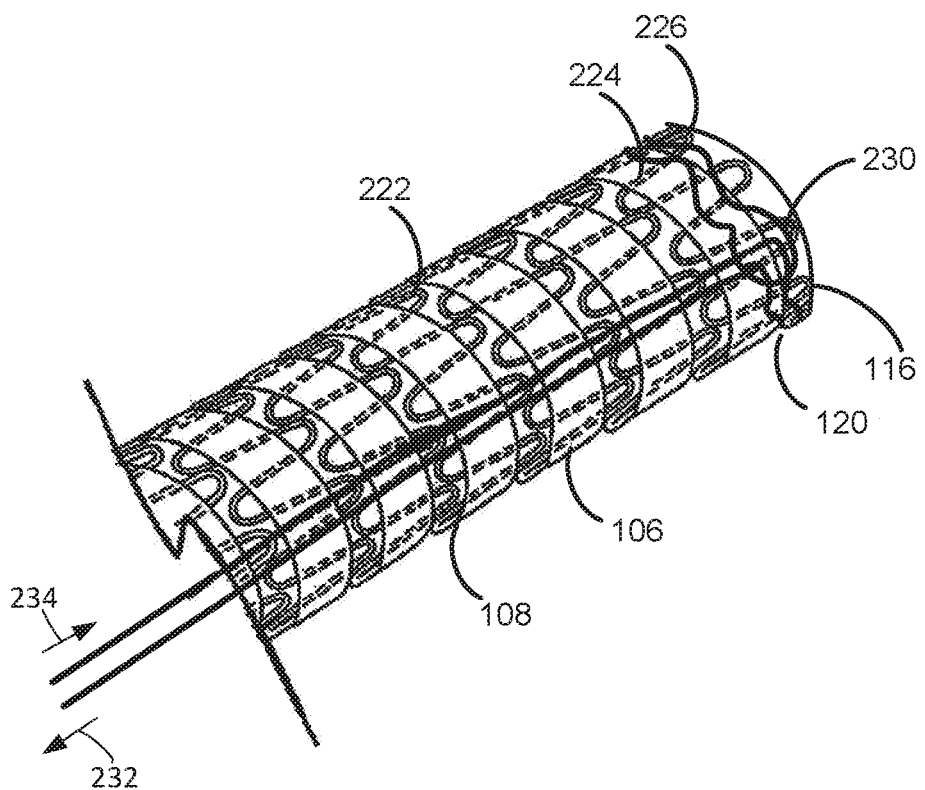
FIG. 2 illustrates a partial perspective view of a medical device in accordance with the present disclosure.

With reference to FIG. 2, in various embodiments, constraining line 120 can interact with stent 106. Stent 106 can comprise a stent pattern 222 having straight segments 224 and apices 226. In various embodiments, constraining line 120 can be woven through alternating straight segments 224 and/or alternating apices 226 around the circumference of expandable implant 104 at the proximal end and perpendicular to a longitudinal axis of expandable implant 104. In other embodiments, constraining line can be woven through straight segments 224 and apices 226 at an angle relative to the longitudinal axis of expandable implant 104. However, constraining line 120 can interact with expandable implant 104 in any manner that will allow constraining line 120 to maintain expandable implant 104 in a desired position and orientation relative to catheter shaft 102.

In various embodiments, expandable implant 104 is inserted into the vasculature of the patient in a collapsed configuration, wherein expandable implant 104 is surrounded by sleeve 110 and held in a desired position relative to catheter shaft 102 by constraining line 120. Expandable implant 104 is then directed to a treatment area of the patient. Upon reaching the treatment area, the implant is deployed. In various embodiments, deployment of expandable implant 104 comprises removing sleeve 110 and removing constraining line 120 from expandable implant 104.

In various embodiments, constraining line 120 can include or form a loop 230. In such embodiments, constraining line 120 can interact with or otherwise extend through the loop 230 to form a slip knot and travel from the proximal end of expandable implant 104 to the outside of the body of the patient. Alternatively, loop 230 can comprise an end loop, such that when constraining line 120 passes through loop 230, it forms a slip knot. In such embodiments, constraining line 120 comprises a line or wire looped into an end loop 230, thereby creating two segments. Both segments pass through loop 230 to form the slip knot, and then travel back along the length of the delivery device and outside of the patient. The resulting slip knot can extend about and releasably restrain the proximal end of the expandable implant 104 axially and/or radially with respect to the catheter shaft 102.

Referring to FIG. 2, to release constraining line 120 from expandable implant 104, the operator can release one of the segments of constraining line 120 and provide tension to the other segment in direction 232. By pulling the non-released segment of constraining line 120, the released segment can travel in the direction 234, through catheter shaft 102, unwind along the segment of expandable implant 104 through which it was woven, then travel back through and exit from catheter shaft 102. Although described in relation to a single constraining line 120 and loop 230, any number of constraining lines 120 and loops 230 are within the scope of the present disclosure.

For example, catheter assembly 100 can further comprise a catheter handle, and one or more segments of constraining line 120 can be removably coupled to the catheter handle. In such embodiments, the catheter handle can comprise a release button that, when activated, releases one segment of constraining line 120.

As illustrated in FIGS. 3A, 3B, 4A, and 4B, constraining line 120 can maintain expandable implant 104 in a desired position relative to catheter shaft 102 and can extend about and constrain the proximal end of the expandable implant 104 relative to the catheter shaft 102.

Figure 3A:
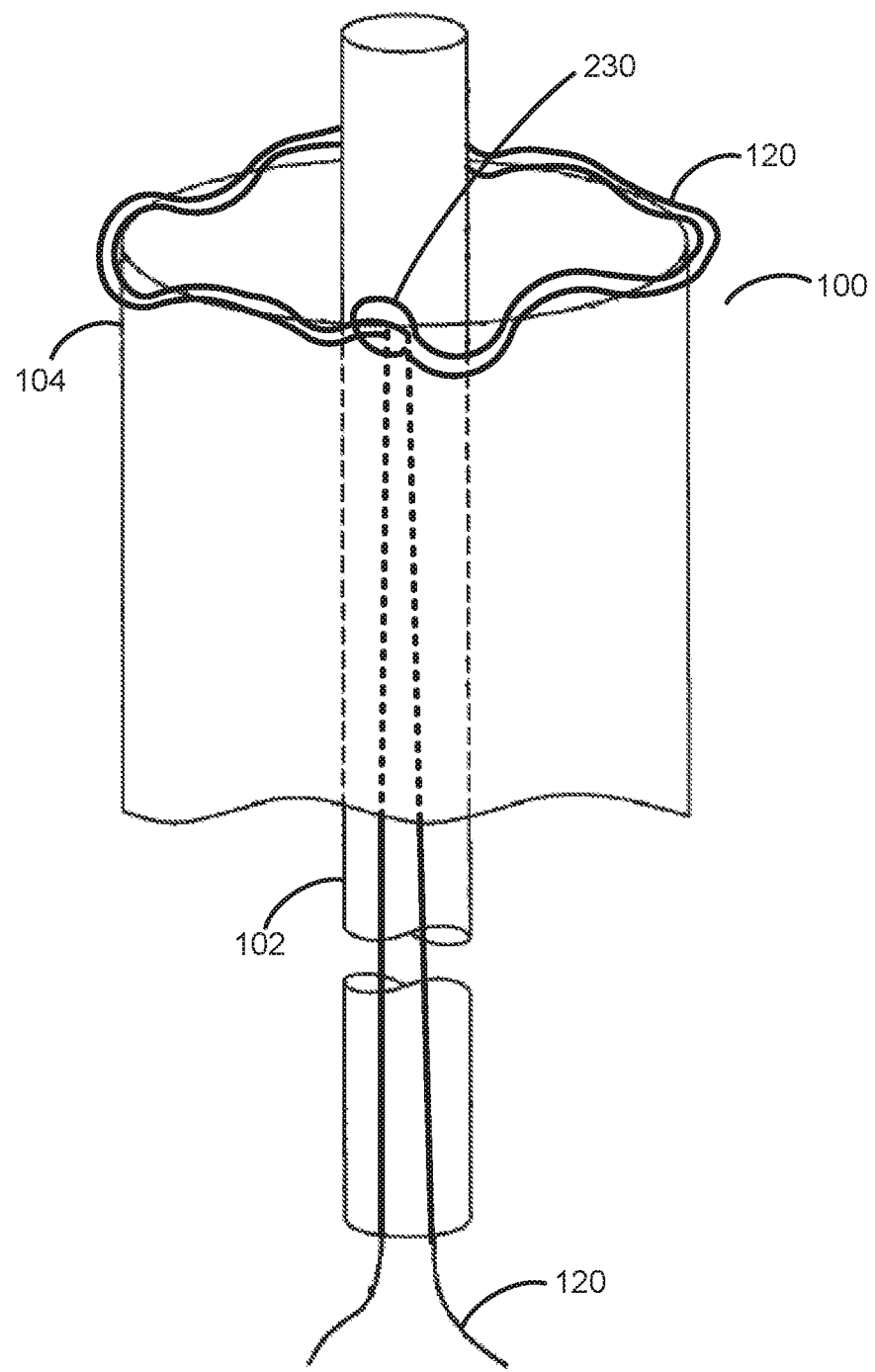
FIGS. 3A and 3B illustrate perspective views of medical devices in accordance with the present disclosure.
Figure 3B:
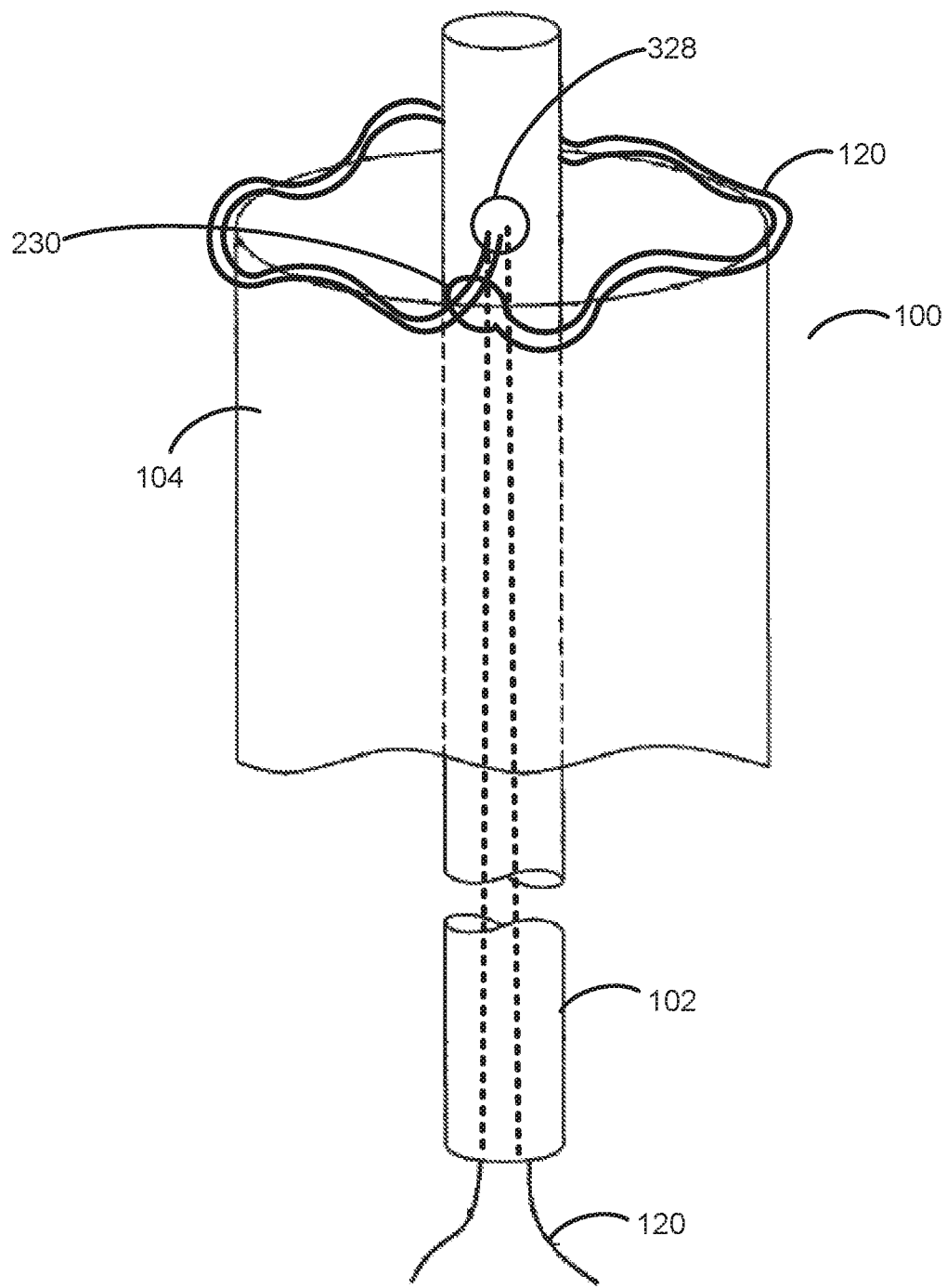

For example, with reference to FIGS. 3A and 3B, expandable implant 104 can be positioned concentrically around catheter shaft 102. As illustrated in FIG. 3A, constraining line 120 can surround the proximal end of expandable implant 104, pass through loop 230 to form the slip knot, and travel along the outside surface of catheter shaft 102. As illustrated in FIG. 3B, after passing through loop 230, constraining line 120 can pass through access hole 328 in catheter shaft 102 and travel along the interior of catheter shaft 102 to the outside of the body of the patient.

Figure 4A:
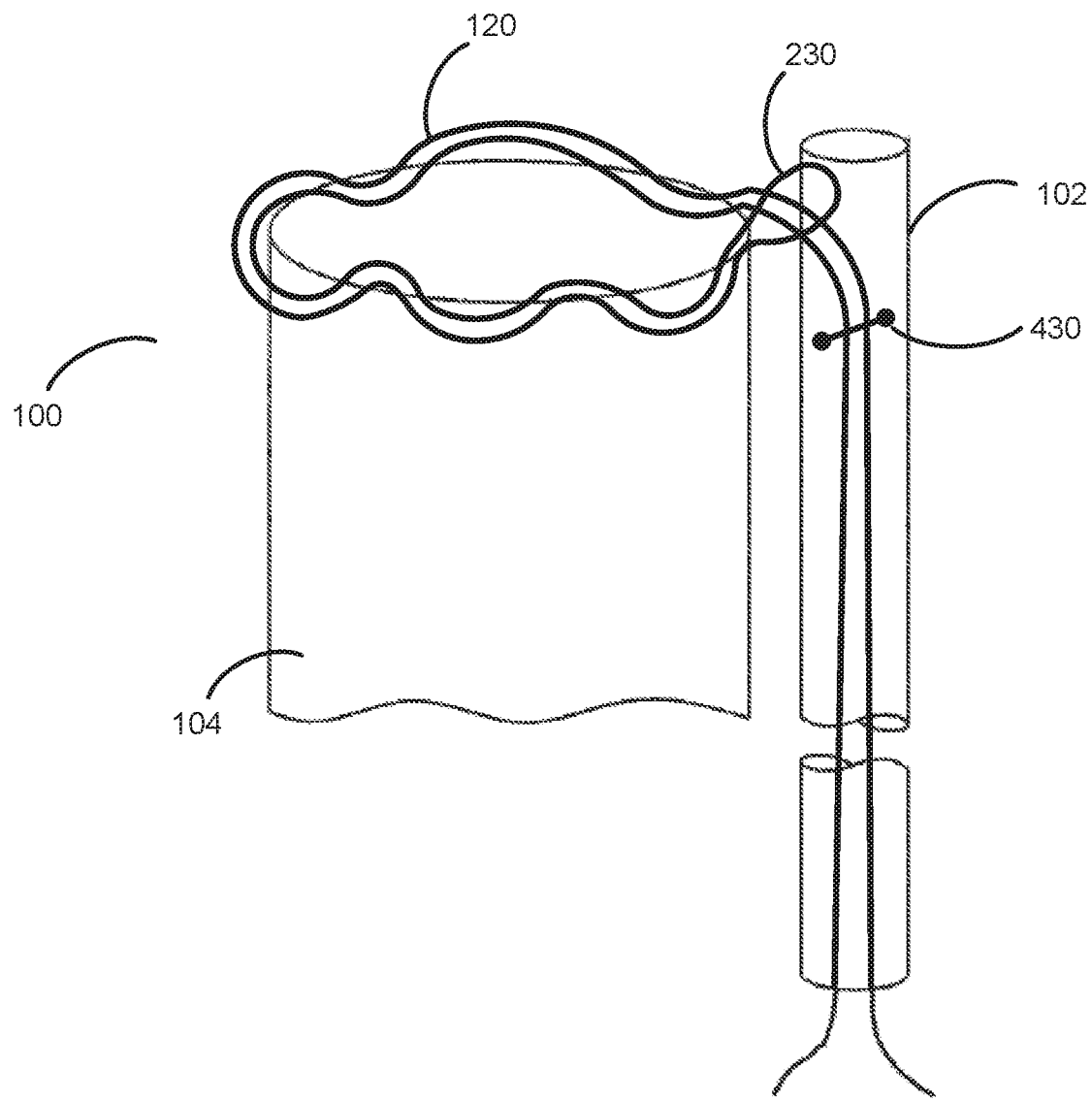
FIGS. 4A and 4B illustrate perspective views of medical devices in accordance with the present disclosure.
Figure 4B:
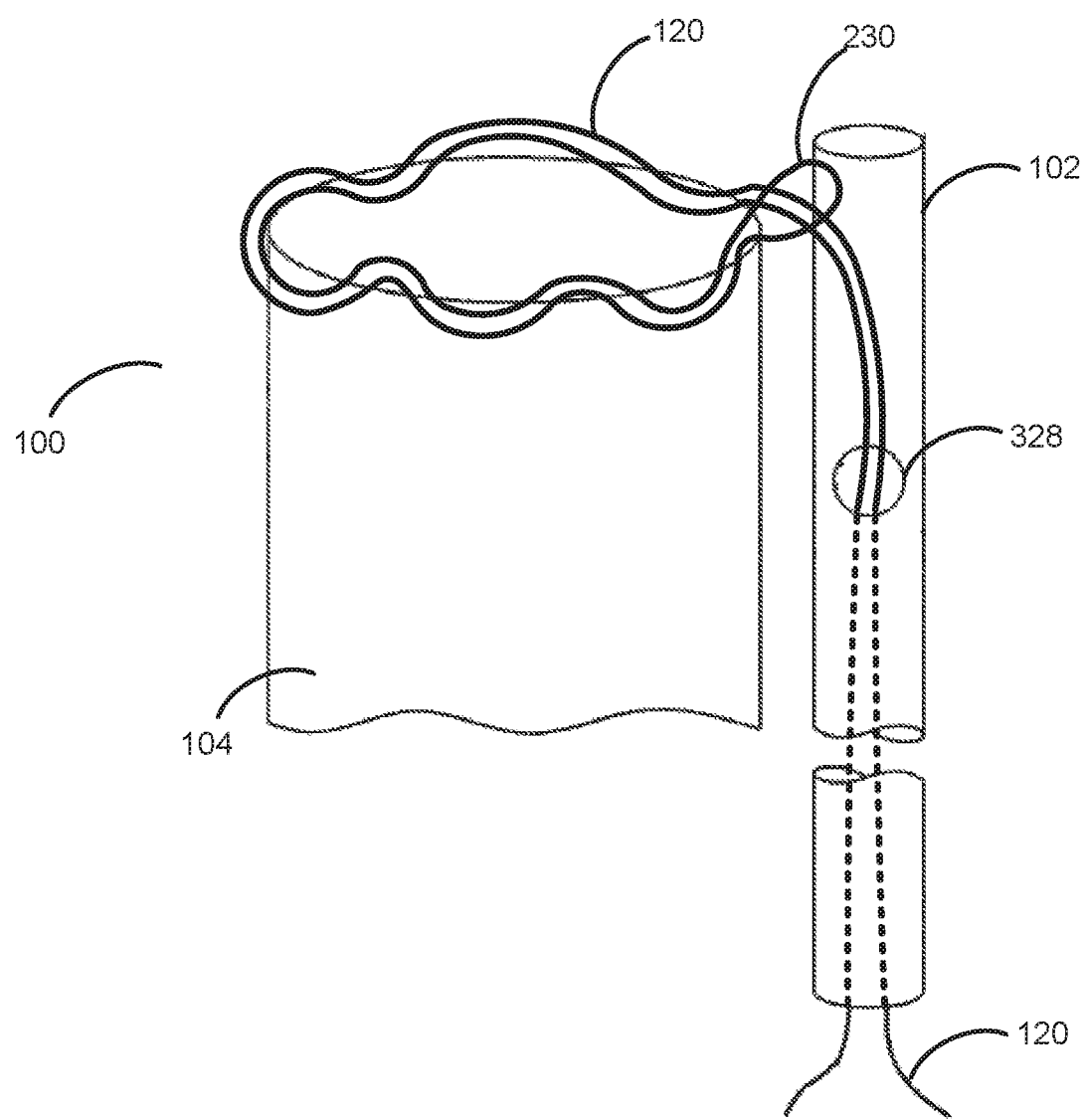

With reference to FIGS. 4A and 4B, expandable implant 104 can be positioned adjacent and parallel to catheter shaft 102. For example, as illustrated in FIG. 4A, constraining line 120 can surround the proximal end of expandable implant 104, pass through loop 230 to form the slip knot, and travel along the outside surface of catheter shaft 102. In various embodiments, catheter shaft 102 can comprise one or more retainers 430, which maintain constraining line 120 in a desired position and orientation relative to catheter shaft 102. As illustrated in FIG. 4B, after passing through loop 230, constraining line 120 can pass through access hole 328 in catheter shaft 102 and travel along the interior of catheter shaft 102 to the outside of the body of the patient. Although the above embodiments are described in detail, any configuration of constraining line 120, catheter shaft 102, and expandable implant 104 is within the scope of the present disclosure.

In various embodiments, constraining line 120 can assist in deployment of expandable implant 104. For example, coupling member 112 can be removed to allow sleeve 110 to open to its unconstrained diameter. Expandable implant 104 can then be expanded to its expanded configuration. In such embodiments, it may be desirable to remove sleeve 110 by applying tension to and consequently retracting sleeve 110 from the body of the patient. However, the tension applied to sleeve 110 can cause portions of stent 106 to collapse, become displaced, or distort. For example, when tension is applied, the proximal end of stent 106 can be pulled towards the distal end, displacing and/or deforming the proximal end. In various embodiments, constraining line 120 can be configured to resist such tension and maintain the proximal end in a desired position and location relative to catheter shaft 102.

In other embodiments, catheter assembly 100 can comprise multiple sleeves. In such configurations, a first sleeve constrains expandable implant 104 in a collapsed configuration. By removing and/or activating a first coupling member, the first sleeve can be removed and expandable implant 104 can expand to a configuration having a larger diameter than in the collapsed configuration.

In such embodiments, expandable implant 104 can be expanded from the collapsed configuration to the intermediate configuration once expandable implant 104 has been delivered near the treatment area of the vasculature of a patient. The intermediate configuration can, among other things, assist in properly orienting and locating the expandable implant within the treatment area of the vasculature.

Catheter assembly 100 can further comprise a balloon. In such embodiments, the balloon can assist in final deployment of expandable implant 104 by, for example, being inflated within expandable implant 104. With sufficient inflation, the balloon can force stent 106 to fully expand against the walls of the vasculature. In embodiments that utilize anchors 116, the balloon can assist anchors 116 in engaging with the vasculature by forcing anchors 116 against the vessel walls.

In accordance with the present disclosure, in various embodiments, a medical device can comprise one or more coatings. In various embodiments, the coatings comprise bio-active agents. Bio-active agents can be coated onto a portion or the entirety of the stent and/or graft member for controlled release of the agents once the device is implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory;

antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In various embodiments, various components of the devices disclosed herein are steerable. For example, during deployment at a treatment site, one or more of the elongated segments can be configured with a removable steering system that allows an end of the elongated segment to be biased or directed by a user. A removable steering system in accordance with various embodiments can facilitate independent positioning of an elongated segment and can provide for the ability of a user to accomplish any of the types of movements previously described, such as longitudinal movement, rotational movement, lateral movement, or angular movement.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical device, comprising:
   a catheter shaft having a distal end, a proximal end, a medial portion between the distal end and the proximal end, and an access opening located in the medial portion of the catheter shaft;
   an expandable implant arranged on the catheter shaft and having a collapsed configuration, an expanded configuration, a proximal end, and a distal end;
   a primary sleeve having a proximal end, a distal end, a first edge and a second edge, the primary sleeve comprising a series of openings, the primary sleeve wrapped around the expandable implant such that the first edge and the second edge are parallel;
   a coupling member engaging the series of openings and releasably securing the primary sleeve to releasably constrain and maintain the expandable implant in the collapsed configuration; and
   a constraining line comprising a first end and a second end that are configured to travel along an interior of the catheter shaft and pass through the access opening to form a primary loop surrounding the distal end of the expandable implant and a secondary loop, wherein the first end and the second end of the constraining line pass through the secondary loop and through the access opening into the catheter shaft such that, when a tension is applied to the expandable implant, the constraining line resists the tension and maintains position of the distal end of the expandable implant with respect to the catheter shaft.

2. The medical device of claim 1, wherein the series of openings extends along the first edge and the second edge from the proximal end to the distal end.

3. The medical device of claim 1, wherein the coupling member releasably secures the first edge and the second edge of the primary sleeve to maintain the expandable implant in the collapsed configuration.

4. The medical device of claim 1, wherein the expandable implant comprises a stent pattern including straight segments and apices, and wherein the constraining line is woven through alternating straight segments or apices around a circumference of the expandable implant.

5. The medical device of claim 4, wherein the constraining line is woven through straight segments or apices at an angle relative to a longitudinal axis of the expandable implant.

6. The medical device of claim 1, wherein the constraining line comprises the secondary loop and wherein the first end and the second end of the constraining line pass through the secondary loop to farm a slip knot.

7. The medical device of claim 1, wherein the first edge and the second edge of the primary sleeve do not contact each other.

8. A medical device comprising:
   a catheter shaft having a distal end, a proximal end, a medial portion between the distal end and the proximal end, and an access opening located in the medial portion of the catheter shaft;
   an expandable implant comprising a collapsed configuration, an expanded configuration, and a proximal end;
   a sleeve having a first edge, a second edge, a first series of openings along the first edge and a second series of openings along the second edge, the sleeve configured to releasably constrain the expandable implant in the collapsed configuration;
   a coupling member woven through the first and second series of openings and configured to releasably secure the first and second edges of the sleeve together to maintain the expandable implant in the collapsed configuration,
   wherein the coupling member is releasable by pulling the coupling member to release the edges of the sleeve and allow the expandable implant to expand from the collapsed configuration to the expanded configuration; and
   a constraining line forming a loop and having a first end and a second end, wherein the first end and the second end of the constraining line are configured to travel along an interior of the catheter shaft, pass through the access opening, and extend through the loop to form a slip knot surrounding the expandable implant,
wherein the slip knot is configured to extend about and releasably restrain the proximal end of the expandable implant with respect to the catheter shaft.

9. The medical device of claim 8, wherein the slip knot is configured to axially restrain the proximal end of the expandable implant.

10. The medical device of claim 8, wherein the slip knot is configured to radially restrain the proximal end of the expandable implant.

11. A medical device, comprising:
a catheter shaft having a distal end, a proximal end, a medial portion between the distal end and the proximal end, and an access opening located in the medial portion of the catheter shaft;
an expandable implant arranged on the catheter shaft and having a collapsed configuration, an expanded configuration, a proximal end, and a distal end; and
a sleeve comprising a series of openings;
a coupling member engaging the series of openings and releasably securing the sleeve to releasably constrain and maintain the expandable implant in the collapsed configuration; and
a constraining line comprising a first end portion and a second end portion that are configured to travel along an interior of the catheter shaft and pass through the access opening to form a primary loop surrounding the distal end of the expandable implant and a secondary loop, wherein the first end portion and the second end portion of the constraining line pass through the secondary loop and through the access opening into the catheter shaft such that, when a tension is applied to the expandable implant, the constraining line resists the tension and maintains position of the distal end of the expandable implant with respect to the catheter shaft.

12. A medical device, comprising:
a catheter shaft having an access opening in a sidewall of the catheter shaft;
an expandable implant arranged on the catheter shaft and having a collapsed configuration, an expanded configuration, a proximal end, and a distal end;
a primary sleeve having a proximal end, a distal end, a first edge and a second edge, the primary sleeve wrapped around the expandable implant such that the first edge and the second edge are parallel, the primary sleeve releasably constraining the expandable implant in the collapsed configuration, the primary sleeve comprising a series of openings extending along the first edge and the second edge from the proximal end to the distal end;
a constraining line comprising a first end and a second end that are configured to travel along an interior of the catheter shaft and pass through the access opening to form a primary loop surrounding the distal end of the expandable implant and a secondary loop, wherein the first end and the second end of the constraining line pass through the secondary loop and through the access opening into the catheter shaft such that, when a tension is applied to the expandable implant, the constraining line resists the tension and maintains position of the distal end of the expandable implant with respect to the catheter shaft; and
a first coupling member engaging the series of openings and releasably securing the first edge and the second edge of the primary sleeve such that the expandable implant is maintained in the collapsed configuration.

13. The medical device of claim 12, further comprising at least one additional sleeve such that the primary sleeve and the additional sleeve form a plurality of sleeves that are concentrically surrounding the expandable implant and configured to deploy the expandable implant in a first stage and a second stage, the first stage comprising releasing at least one of the plurality of sleeves to a configuration suitable to constrain the expandable implant only to an intermediate configuration, and the second stage comprising removing a remainder of the plurality of sleeves from the expandable implant to release the expandable implant to the expanded configuration.

14. The medical device of claim 13, further comprising a plurality of coupling members engaging with the plurality of sleeves such that disengaging the plurality of coupling members causes the plurality of sleeves to be released from the expandable implant in the first and second stages.

15. A medical device, comprising:
a catheter shaft having an access opening in a sidewall of the catheter shaft;
an expandable implant arranged on the catheter shaft and having a collapsed configuration, an expanded configuration, a proximal end, and a distal end;
a primary sleeve having a proximal end, a distal end, a first edge and a second edge, the primary sleeve wrapped around the expandable implant such that the first edge and the second edge are parallel, the primary sleeve releasably constraining the expandable implant in the collapsed configuration;
a constraining line comprising a first end and a second end that are configured to travel along an interior of the catheter shaft and pass through the access opening to form a primary loop surrounding the distal end of the expandable implant and a secondary loop, wherein the first end and the second end of the constraining line pass through the secondary loop and through the access opening into the catheter shaft such that, when a tension is applied to the expandable implant, the constraining line resists the tension and maintains position of the distal end of the expandable implant with respect to the catheter shaft;
at least one additional sleeve such that the primary sleeve and the additional sleeve form a plurality of sleeves that are concentrically surrounding the expandable implant and configured to deploy the expandable implant in a first stage and a second stage, the first stage comprising releasing at least one of the plurality of sleeves to a configuration suitable to constrain the expandable implant only to an intermediate configuration, and the second stage comprising removing a remainder of the plurality of sleeves from the expandable implant to release the expandable implant to the expanded configuration; and
a plurality of coupling members engaging with the plurality of sleeves such that disengaging the plurality of coupling members causes the plurality of sleeves to be released from the expandable implant in the first and second stages.

* * * * *